United States Patent [19]

Taube

[11] Patent Number: 4,889,116
[45] Date of Patent: Dec. 26, 1989

[54] ADAPTIVE CONTROL OF NEONATAL FRACTIONAL INSPIRED OXYGEN

[75] Inventor: John C. Taube, Philadelphia, Pa.

[73] Assignee: Phospho Energetics, Inc., Philadelphia, Pa.

[21] Appl. No.: 121,501

[22] Filed: Nov. 17, 1987

[51] Int. Cl.$^4$ .................. A61M 16/00; A62B 7/00; F16K 31/02

[52] U.S. Cl. .................. 128/204.23; 128/634

[58] Field of Search .................. 128/716, 725, 204.23, 128/204.14, 633–634

[56] References Cited

U.S. PATENT DOCUMENTS 4,326,513  4/1982  Schulz et al. .................. 128/204.23
4,765,340  8/1988  Sakai et al. .................. 128/716

Primary Examiner—Francis Jaworski
Assistant Examiner—George Manuel
Attorney, Agent, or Firm—Caesar, Rivise, Bernstein, Cohen & Pokotilow, Ltd.

[57] ABSTRACT

An adaptive controller for delivering fractional inspired oxygen to a patient. The controller utilizes a pulse oximeter connected by an optical sensor to the patient for measuring the patient's blood hemoglobin saturation and pulse rate. Signals from the oximeter are used by a calculator for determining the fractional inspired oxygen level to be delivered to the patient. The calculated percentage of oxygen is provided to the patient so that the gas taken in by the patient automatically causes the blood in the patient to reach a predetermined hemoglobin saturation level which adapts to the patient's requirements. The calculator is programmed to determine when there is an excess deviation of the patient's pulse rate. When an excess deviation is detected, the fractional inspired oxygen level to the patient is fixed until the excess deviation of the pulse rate has been terminated. A depressed respiration level can also be detected which causes a preset higher percentage of oxygen to be supplied to the patient until the depressed respiration of the patient has been terminated.

7 Claims, 4 Drawing Sheets

MOVEMENT DETECTION

*APNEA DETECTION*

ADAPTIVE CONTROL OF NEONATAL FRACTIONAL INSPIRED OXYGEN

BACKGROUND OF THE INVENTION

This invention relates generally to continuous positive airway pressure ventilation systems such as respirators and in particular to a new and useful non-invasive adaptive controller of blood system oxygen. The system has particular application in the adaptive control of neonatal fractional inspired oxygen ($FiO_2$) and is intended to make more automatic the control of oxygen to the patient whether the patient be neonatal or mature.

This system utilizes a pulse oximeter to optically determine hemoglobin saturation of the patient's blood and use this information to regulate oxygen delivered to the patient's breathing mask or hood. The control mechanism is derived from the known relationship between the minimum required $FiO_2$ delivered to the patient and predetermined lung function dynamics in order to maintain a desirable arterial blood hemoglobin saturation level (HSAT).

The use of a pulse oximeter permits non-invasive determination of a patients arterial blood hemoglobin saturation and pulse rate. From the measured hemoglobin saturation and pulse rate a non-invasive determination of pulse rate and blood pressure parameters can be used to determine patient movement and apnea to suspend and correct, respectively, the operation of the system without requiring operator intervention.

DESCRIPTION OF THE PRIOR ART

Devices for controlling the oxygen content of the blood by controlling the inspired oxygen delivery to a patient are well known. U.S. Pat. No. 2,414,747 issued to Harry M. Kirschbaum on Jan. 21, 1947 shows a method and apparatus for controlling the oxygen content of the blood of living animals which discloses control of blood oxygen content by the use of an ear oximeter which produces a signal used to control the proportion of inspired oxygen. By directing a beam of light through a capillary bed, as in the ear, the characteristics of the light become modified by the color of the blood that intercepts its path. Thus, the change in oxygen levels of the blood can be detected non-invasively where signals can be generated, amplified and used to control the oxygen supply delivered to a patient.

Numerous improvements have been made since that time wherein better matching of oxygen delivery to the needs of the patient have been made such as shown in U.S. Pat. No. 3,734,091 to Ronald H. Taplin issued on May 22, 1973. Taplin discloses an optical oximeter and a temporary oxygen-deficient mixture (anoxic) to control blood oxygen saturation. Thus, to prevent super saturation, or more than a 100% oxygen saturation, Taplin dicloses limiting the oxygen by proving the anoxic mixture each time the saturation of the blood reaches a predetermined percentage level.

An invasive patient data controlled respiration system is shown in U.S. Pat. No. 4,326,513 of Volker Schultz, et al, issued on Apr. 27, 1982 which shows a patient data controlled respiration system utilizing sensed concentration of oxygen in the patient's blood to control a respirator supplying breathing air having the selected concentration of oxygen to the patient. In such a system, a sensor is connected to the patient for sensing arterial partial pressure of the patient's blood ($PaO_2$).

The system further includes a minimizing comparator which has preset threshold levels and determines whether the $FiO_2$ value is above or below those threshold values. When a transient $FiO_2$ value rises above or drops below the threshold value, it causes the control device to cancel the adjustment to the inspired oxygen and causes the previous amount of oxygen to be supplied to the patient. In this way, there can be only small changes in the original $FiO_2$.

The prior art is however, devoid of a non-invasive relatively inexpensive system for the control of oxygen delivery which will detect patient movement to suspend adaptive control of the oxygen supplied to the patient and will provide a corrective amount of oxygen to the patient when apnea is detected. Both of these features are vital when controlling oxygen supply to an infant because hypoxia and apnea both can cause irreparable harm to an infant as well as a more mature patient.

OBJECTS OF THE INVENTION

It is therefore an object of the invention to provide a new and useful adaptive control of neonatal fractional inspired oxygen.

Another object of the invention is to provide a new and improved respiration system which automatically provides fractional inspired oxygen to a patient to provide the highest percentage of oxygen saturation in the blood while maintaining the lowest possible addition of oxygen to the atmosphere that the patient is breathing.

Still another object of the invention to provide a new and improved controller of fractionally inspired oxygen which utilizes a pulse oximeter to take advantage of its unique ability to accurately determine peak arterial oxygen levels and more accurately derive a fractionally inspired oxygen level which better matches the need of a patient.

Still another object of the invention is to provide a new and improved controller of fractionally inspired oxygen which suspends adaptation of the $FiO_2$ during patient movement.

Yet another object of the invention is to provide a new and improved controller of fractionally inspired oxygen to a patient which detects apnea and causes a resultant change of the oxygen level to a predetermined level until the detection of apnea has terminated.

These and other objects of the invention are achieved by providing an adaptive controller for delivering fractional inspired oxygen to a patient. The controller comprises an oximeter connected by an optical sensor to the patient for measuring the patient's blood hemoglobin saturation and pulse rate. The oximeter generates signals representative of the blood hemoglobin saturation and the pulse rate. Calculation means are provided which are responsive to the signals from the oximeter for determining the fractional inspired oxygen level to be delivered to the patient. A source of oxygen and a source of air are provided for combining or mixing the oxygen and the air. The means for mixing is controlled by calculation means to provide a calculated percentage of oxygen and has an output connected to the patient so that the gas taken in by the patient automatically causes the blood in the patient to reach a predetermined hemoglobin saturation level which adapts to the patient's requirements. The calculation means also includes means for determining an excess deviation of the patient's pulse rate. The means for determining the excess deviation causes the output of the calculation means to fix the fractional inspired oxygen level to the patient until the excess deviation of the pulse rate has been terminated. The calculation means also includes a depressed respiration level detector which causes the means for mixing to provide to the patient a preset higher percentage of oxygen to the patient until the depressed respiration of the patient has been terminated.

Other objects and many of the attendant advantages of this invention will be readily appreciated as the same becomes better understood by reference to the following detailed description when considered in connection with the accompanying drawing.

DETAILED DESCRIPTION OF THE PREFERRED EMBODIMENT

Figure 1:
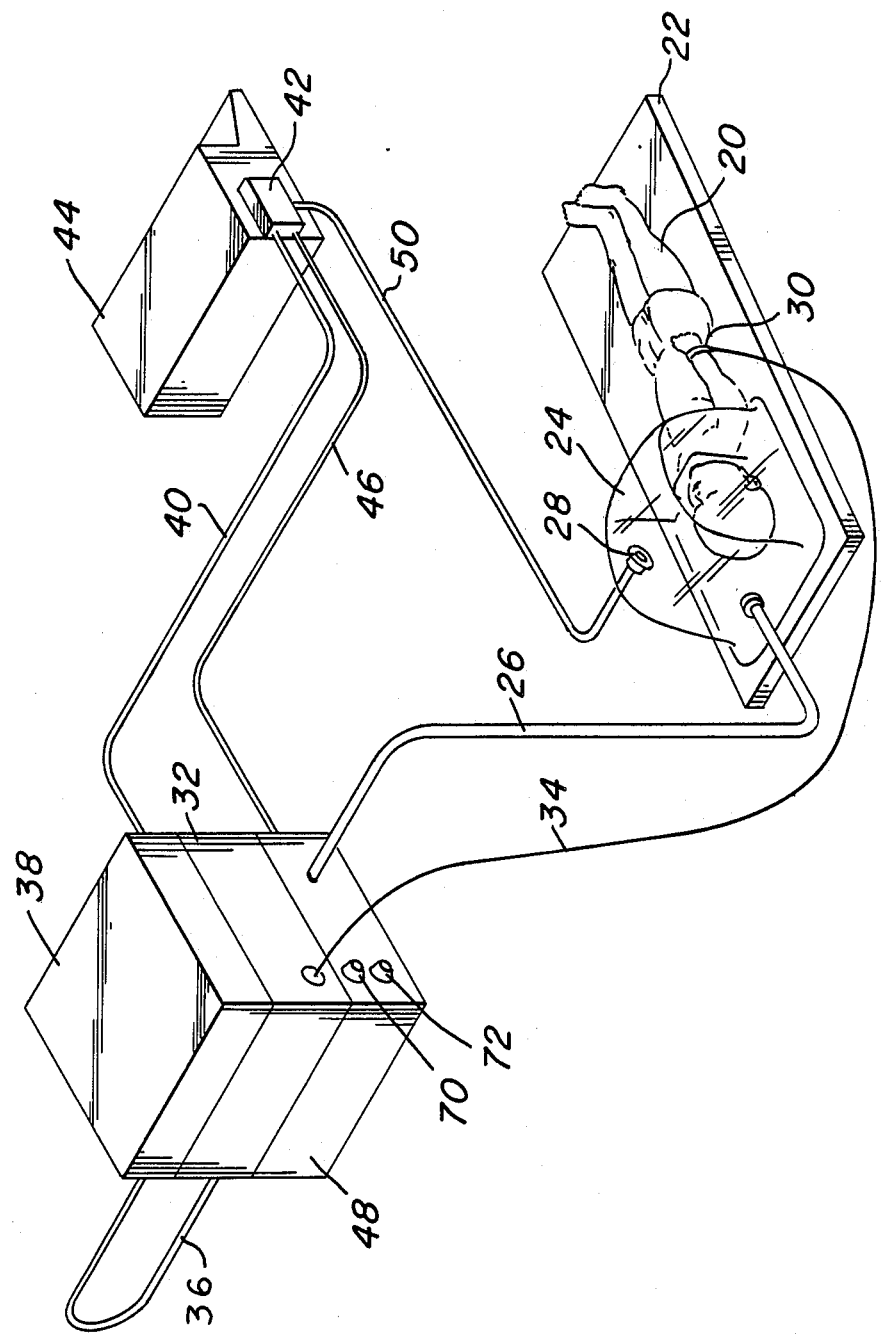
FIG. 1 is a diagrammatic perspective representation of an adaptive controller of neonatal fractional inspired oxygen system embodying the invention.

Referring now in greater detail to the various figures of the drawings wherein like reference characters refer to like parts, an adaptive controller of neonatal fractional inspired oxygen is shown in FIG. 1 for the purpose of providing fractional inspired oxygen to an infant 20. The infant 20 is shown lying on a matress 22 having a hood 24.

The hood controls the breathing environment of the infant and includes an input port connected to tube 26 which delivers fractional inspired oxygen to the patient. A sensor 28 is connected to the hood 24 for detecting the percentage of oxygen in the atmosphere surrounding the infant's respiratory track.

An optical sensor 30 is placed on the patient's finger. The sensor 30 includes a wrist strap for securing the sensor to the patient.

The system also includes a pulse oximeter 32 of the type made by Nellcor Incorporated, of Haywood, Calif. and which is shown in U.S. Pat. No. 4,653,498 issued on Mar. 31, 1987. Pulse oximeter 32 is connected by a fiber optic cable 34 to the sensor 30.

The pulse oximeter is connected via a fiber optic cable 36 to an interface 38. The interface as will hereinafter be seen in greater detail converts the digital signals provided in fiber optic form from the pulse oximeter to analog signals which are provided via lines 40 to an analog/digital converter 42.

The analog/digital converter is mounted upon the mini computer 44. The mini computer's outputs are connected via the analog/digital converter 42 and then via lines 46 to a mixer 48.

Finally, the sensor 28 is connected to the analog/digital converter 28 by wires 50. As will hearinafter be seen, the sensor 28 is not a part of the circuitry which is used to control the fractional inspired oxygen provided to the patient 20. The signals on line 50 which are representative of the oxygen in the hood 24, are connected via the anolog/digital converter to circuitry provided in the minicomputer which is used for setting an alarm if the oxygen is either too high or too low. The limits are set in the software of the minicomputer 44.

Figure 2:
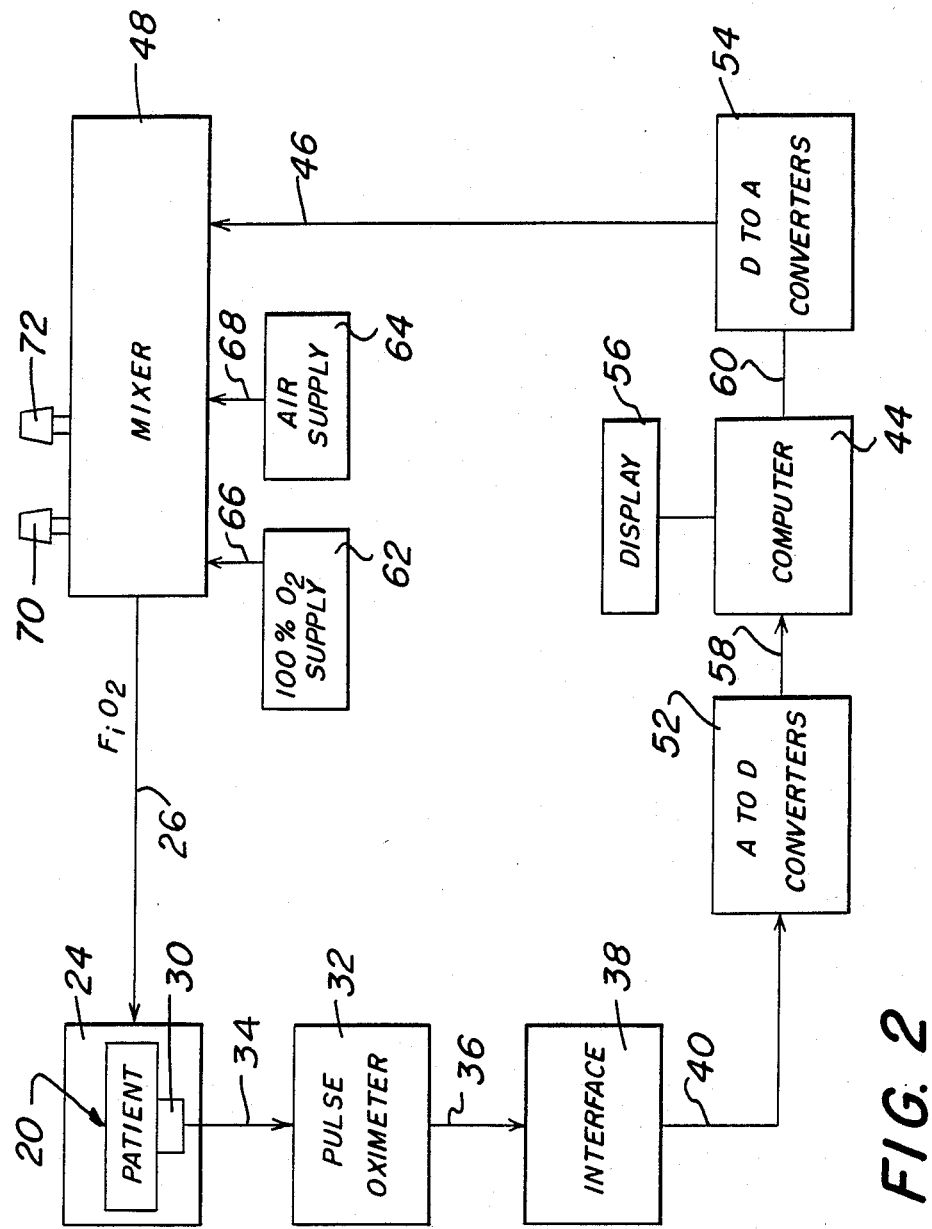
FIG. 2 is a schematic block diagram of the invention.

The connections of the various components of this system are best understood in connection with the schematic block diagram shown in FIG. 2.

As seen in FIG. 2, the sensor 30 is attached to patient 20 sensor and is connected via the fiber optic cable 34 to the pulse oximeter 32. The pulse oximeter 32 determines from the optical sensing of the patient the pulse strength, hemoglobin saturation and pulse rate. The values of all three of these parameters are digitally displayed on the front face of the pulse oximeter in digital form by suitable displays (not shown). The pulse oximeter 32 transfers in digital form over fiber optic cable 36 to the interface 38 the digital representations of the pulse strength, hemoglobin saturation (HSAT) and pulse rate. The interface 38 converts the digital signals provided via the fiber optics cable 36 into electrical signals on wires 40 which are analog signal representations of the pulse strength, hemoglobin saturation and pulse rate.

The wires 40 are connected to analog to digital converters 42 which are part of an analog/digital converter 42 which also includes digital to analog converter 54. The analog/digital converters 52 convert the analog signals into the digital form required for use on minicomputer 44. The minicomputer 44 preferably comprises a Compaq personal computer which is IBM compatible and which includes a display 56 and which may also be connectable to a suitable printer (not shown). The output of the analog/digital converter 52 is provided to the minicomputer 44 via lines 58. The minicomputer 44 utilizes the hemoglobin saturation and pulse rate which are provided in digital form on lines 58 for determining the appropriate percentage of oxygen to provide to the patient or infant to produce the highest obtainable patient blood hemoglobin saturation level with a minimum of oxygen necessary to be added to the air supply having a 21% oxygen concentration.

The signal representative of the appropriate $FiO_2$ is provided in digital form via lines 60 to the digital to analog converter 54 of analog/digital converter 42. The digital to analog converter provides the signals to mixer 48 via lines 46 which control the proportion of oxygen supplied to the patient. A pure oxygen supply source 62 and an air supply 64 containing a 21% oxygen concentration are both provided which are connected via tubes 66 and 68 respectively to the mixer 48. Conventional solenoid control is used for the purpose of proportioning the air in accordance with the signals provided on lines 46 from the digital to analog converter. Accordingly, the appropriate mixture of oxygen in the air is provided via tube 26 to the patient. The mixer 48 also has attached thereto a pair of manual knobs 70 and 72 which are connected to the oxygen supply 62 and air supply 64 respectively. The knobs enable manual regulation by physician or operator to provide 20 to 30 PSI of pressure of both supplies to the mixer.

The Compaq minicomputer contains an 8088 microprocessor which is controlled by program modules to determine $FiO_2$. The program used for determining the proper proportion of oxygen to be provided to the patient is shown in the attached Exhibit A. The program is written in C specifically for a Compaq IBM PC compatible.

In addition to the program module for provideing the adaptive control of oxygen to the patient there is shown in Exhibit B a program module written in C for the Compaq minicomputer which includes two programs, one used for determining movement of the patient and the other to detect apnea.

Figure 3:
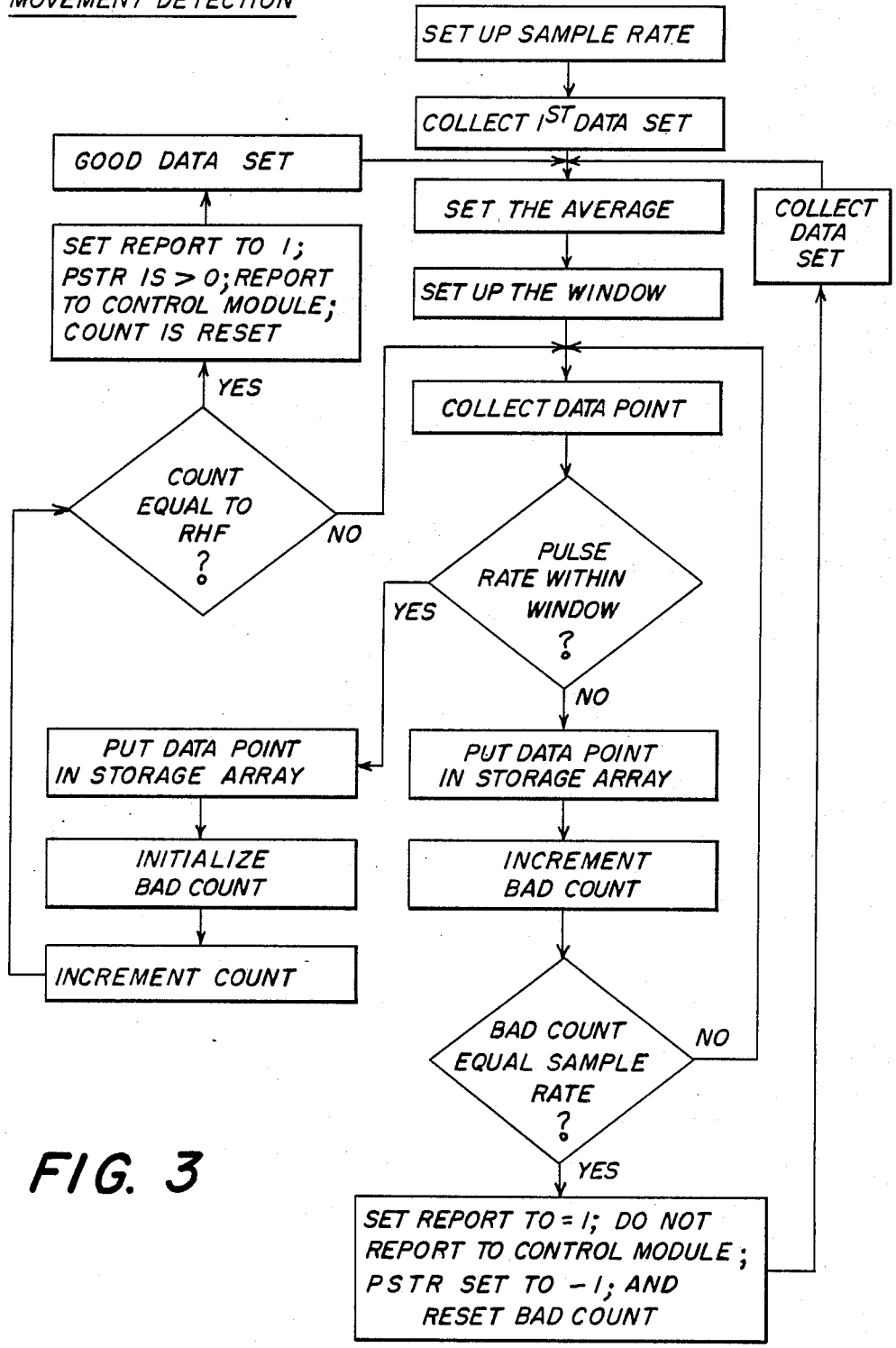
FIG. 3 is a flow diagram showing the operation of the programmed microprocessor for detecting movement and suspending change of the fractional inspired oxygen until the movement has been stopped.

Referring to FIG. 3, the movement detection program flow diagram is shown. As a preface to the steps of the computer program, it should be understood that the clock in the minicomputer is set to record all of the data provided by the pulse oximeter from the patient to the computer once each second. It will be remembered that the following data points are provided by the pulse oximeter to the computer, namely, the pulse strength, the hemoglobin saturation and the pulse rate. Thus, once each second, the minicomputer will have recorded in it the data points for the pulse strength, the hemoglobin saturation and the pulse rate. Where the sample rate is 10 seconds, the computer will collect 10 data points for each one of these perameters. Accordingly, the description of the operation of the movement detection program is as follows:

1. The sample rate is selected.
2. The computer collects the first data set and stores it.
3. The computer then determines the average value for pulse rate. If the sample rate selected is 10 seconds the computer collects 10 data points of the pulse rate which are added and divided by 10 to provide an average of the pulse rate for these 10 data points.
4. The computer then forms a window of 12 beats per minute (BPM) around the average pulse rate value. This means that if the pulse rate were 72, the window would be from 60 to 84 because the upper limit is the average value plus 12 beats per minute and the lower limit is the average value minus 12 beats per minute.
5. After completing the previous steps 2 to 4 above, the program microprocessor compares the next incoming data point of pulse rate to determine whether the pulse rate is within the window determined in step 4.
6. If the incoming pulse rate data point is within the window, the program causes the microprocessor to store the pulse rate in memory, resets a bad data counter to 0 and increments a good data counter by 1.
7. If the incoming pulse rate data point is not within the window, then the computer stores the data point in memory and increments the bad data counter by 1.
8. If at any time the good data counter equals the sample rate selected in step 1 above, the microprocessor sends all data points for all of the parameters previously stored during step 2 above from the microprocessor memory to a data memory file on a floppy disk. The computer microprocessor also sends a signal which is representative of the hemoglobin saturation value to the oxygen control program module, Exhibit A, within the control program thus changing the oxygen concentration delivered to the patient. The good and bad data counters are also reset to 0.
9. The computer microprocessor then collects a new data set and restarts the loop previously described in steps 3 to 7, above.
10. If the bad data counter at any time equals the sample rate set in step 1 above, the computer microprocessor sends all data points recorded during step 2 above to a data memory file which is also stored on a floppy disk. However, the microprocessor does not send a signal representative of the hemoglobin saturation to the oxygen control module within the control program of Exhibit A. Thus, there is no change of the percentage of oxygen provided to the patient and the bad and good data counters are reset to 0.
11. The computer then starts again with a new set of data points and restarts the control loop previously described in steps 3 to 7 above.

It can therefore be seen that until a good data set is again received the hemoglobin saturation value is not sent to the oxygen control module within the control program and thereby does not change the oxygen concentration delivered to the patient. Thus, the adaptive control of fractional inspired oxygen is suspended until such time as the patient has stopped moving and the pulse rate is therefore again within the window. Therefore, the percentage of oxygen in the $FiO_2$ remains fixed until the movement of the patient has stopped.

The most important reason for stopping the adaptation of the control of the oxygen supply to the patient is to prevent an over saturation of the blood with oxygen and to prevent hypoxia, which is extremely dangerous to a patient, particularly an infant.

This invention thus effectively prevents hypoxia while permitting automatic adaptive control of fractional inspired oxygen. This feature is enabled by creation of the floating window to determine whether the incoming pulse rate shows any movement of the patient.

By detecting movement of the patient, a movement of the patient cannot cause a poor signal generated by the sensor 30 from triggering a chain of sequences which results in the sending of too much oxygen to the patient.

Figure 4:
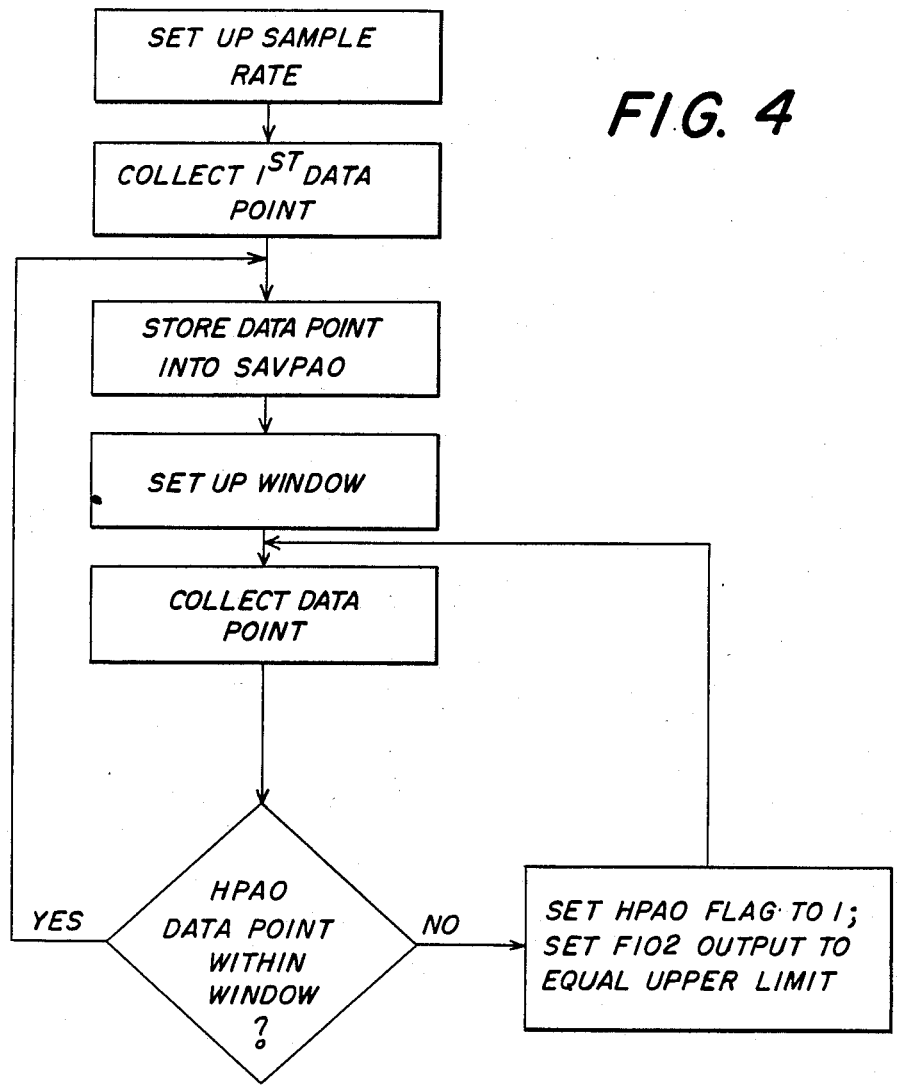
FIG. 4 is a flow diagram showing the operation of the programmed microprocessor for apnea detection.

The flow diagram of operation of the programmed microprocessor to detect apnea in shown in FIG. 4. The detection of apnea is, of course, also critical in an automatic system. In addition to the operation of the detection and control of $FiO_2$ which is accomplished by the microprocessor as shown to be programmed in FIG. 4, it should also be understood that suitable audible and visible alarms are also used which are set off when apnea is detected.

The steps of operation shown in FIG. 4 are as follows:

1. The operator or physician sets up the sample rate in the same manner explained above with respect to FIG. 3.
2. The microprocessor generates the first data point of blood partial pressure of oxygen ($PaO_2$). The $PaO_2$ is calculated by the microprocessor from the value of the patient's blood hemoglobin saturation (HSAT).
3. The microprocessor then stores the data point of $PaO_2$ in memory.
4. A window is next formed around the $PaO_2$ data point stored in memory by making the window 6 mm Hg (millimeters of mercury) above and below the data points stored in memory. e.g., the upper limit equals the data point +6 mm Hg, the lower limit equals the data point −6 mm Hg.
5. The computer then generates a new data point from the HSAT which is the next calculated value of $PaO_2$.
6. The new $PaO_2$ data point is compared with the window to determine whether it falls within the window.
7. If the $PaO_2$ falls within the window, defined in step 4 above, the computer stores the new data point in memory and the loop continues again through steps 4 to 7.
8. If the new $PaO_2$ data point is not within the window the microprocessor sends a signal to the control program for setting the oxygen delivered to the patient, to the maximum level, referred to as "UPPER LIMIT". This value is determined by the physician when the system is turned on and entered via the keyboard of the minicomputer.

The computer microprocessor saves the previously stored data point that is in memory which had previously determined the FiO$_2$ delivered to the patient and discards the bad data point (which is out of the window). A new PaO$_2$ data point is generated and the steps 6 to 8 above, are repeated.

In the overall operation of the system, the pulse oximeter 32 and the mixer 48 as well as the minicomputer are connected as shown in FIG. 1 to the patient. The pulse oximeter 32 is turned on and the patient's hemoglobin saturation is monitored by the attending physician. The breathing gas oxygen percentage is manually controlled by knobs 70 and 72 which are part of manually controlled valves provided on the mixer 48. The knobs are adjusted until the physician can obtain the highest obtainable patient blood hemoglobin saturation level displayed by the pulse oximeter 32. The physician then lowers the breathing gas oxygen concentration provided via tube 26 to the point where the HSAT begins to reduce in order to determine the minimum level of oxygen in the breathing gas that the patient needs to maintain a desired blood hemoglobin saturation level.

The physician then enters the desired HSAT for the patient via the keyboard of the mini computer 44. The oxygen control system is then started by inserting the appropriate instruction on the keyboard. The breathing gas oxygen level is then controlled automatically by the patients hemoglobin saturation signals from the pulse oximeter 32.

When an infant moves, the movement can cause the pulse oximeter to release hemoglobin saturation signals that are not consistent with the actual blood oxygen values. This condition is detected by the movement detection program in the minicomputer 44 which monitors the pulse rate of the patient. When patient movement is detected, the breathing gas mixture or percentage of oxygen is appropriately controlled so that the breathing gas mixture remains at a value prior to the movement and a visual display generates an alarm on the screen of the minicomputer. Of course, an audible alarm and remote alarm (not shown) can be provided where required.

When the minicomputer has determined that the patient is no longer moving and the hemoglobin saturation signal is correct for the patient, the minicomputer releases the breathing gas mixture control signal which prevented regulating the breathing gas oxygen level at a point prior to the movement.

Similarly, the minicomputer 44 continuously monitors the patient for apnea. When detection of apnea has occured, the minicomputer causes the breathing gas oxygen level to be set at a level determined by the physician prior to the apnea event. This is done automatically and the patient receives the predetermined level of oxygen previously set by the attending physician.

The display of the computer displays the word apnea during the time that apnea is detected. Other suitable alarms such as audible and remote may also be provided.

It can therefore be seen that a new and improved adaptive control system for fractional inspired oxygen has been provided.

The system takes advantage of the unique ability of a pulse oximeter to accurately determine peak arterial oxygen levels. This enables the control system to accurately derive a fractional inspired oxygen level which better matches the needs of the patient. In addition, the detection of a pulse rate which corresponds to movement of the patient is accomplished with a movable window. The movable window is of course the window formed about the most recent pulse rate of the patient. This permits an adaptation of the pulse rate while the fractional inspired oxygen provided to the patient is being adaptively controlled.

In addition, by use of the parameters provided to the mincomputer by the pulse oximeter, determination of PaO$_2$ is enabled, thereby enabling the unit to detect apnea.

Both the movement and the apnea detection by automatic non-invasive techniques further makes the system inexpensive both to manufacture as well as to use. It further increases the state of the art in providing more automation in matching the patient's adapting needs for oxygen while providing the patient with considerable protection against hypoxia and apnea.

Without further elaboration the foregoing will so fully illustrate my invention that others may, by applying current or future knowledge, adopt the same for use under various conditions of service.

---

Exhibit A

Controller program - see ox.txt for details.
       J. Mills   Phospo Eneretics   1986 06 13
       C Copyright, Phospho energetics 1986.

```
For this version, the initial value of km (k1) is accepted
from OX (80/foxy). The program asks for the lung time
constant, tl, and the value overrides that from OX (foxy).
km is adjusted slowly from the ratio pao/uic, when conditions
are steady.
*/
#include "defs.h"
void con(ccon, drcon, mst, cst)
float ccon[ ], drcon[ ], mst[ ], cst [ ];
{
        float pahsat( );
        void setpar( );
        static float olderr, shpao, bakpao;
        static int count, source;
        float apao, error, rf, enmr;
        char answ;
/****************** INITIALISATION ******************/
        if (rnd(inflag) = = -1)   /* Initialise */
        {
                km = k1;
        printf("Control from pulse oximeter (p) or brain oximeter (b) #");
                scanf("%c", &answ);
                if (answ = = 'b') source = 0;
                    else source = 1;
                printf("Lung time constant, secs. #");
                scanf("%f", &tl);
                setpar(ccon, cst); /* Calculate gain consts. */
                inter = foxy; /* set integrator state */
                rpao = pahsat(ref); /* Reference PaO2 */
        }
        if (rnd(inflag) <0) /* Initialise or re-initialise */
        {
                shpao = 0.0;
                count = 0;
                olderr = 0.0;
                bakpao = 9999;
        }
/****************** RUN CONTROLLER ******************/
/* On manual control, track ui with inter */
        if(rnd(inflag) = = 1) inter = 0.7 * inter + 0.3 * ui;
/* Adaptation on manual or automatic control */
        if(rnd(inflag) > = 0)
        {
                if (source) apao = hpao;
                    else apao = bpao;
                if (apao > 0.0)
                {
                        if (fabs(bakpao - apao) <5 && ui >5)
```

Exhibit A (continued)

```
                /* steady */
                {
                    km = 0.90 * km + 0.10 * (apao/ui);
                    setpar(ccon, cst); /* Adaptation */
                }
                bakpao = apao;
            }
        }
    /* Automatic control */
        if(!rnd(inflag))
        {
            if (apao > 0.0)
            {
                error = rpao — apao;
                inter += kint * error;
                uic = kprop * error + inter + kder *
                    (error — olderr);
                if (uic > uiclimit) uic = uiclimit;
                if (uic < noxy) uic = noxy;
                olderr = error;
                shpao += apao;
                count++;
            }
            if (npao > 0.0) /* NMR signal available */
            {
                shpao /= count; /* Average hpao */
                if (nmr >0.4 && fabs(shpao — rpao) < 10.0)
                                /* useful values */
                {
                    enmr = nmr + (rpao — hPao)/41.7;
                            /* est nmr if hpao=rpao */
                    rf = sqrt(count*hf) * 0.013;
                                /* 0.1 if nmr period 60 */
                    rpao = (1.0—rf) * rpao + rf * rpao *
                        refn/enmr;
                }
                shpao = 0.0;
                count = 0;
            }
        }
    }
/****************** Set gain parameters ******************/
setpar(ccon. cst)
float ccon[ ], cst [ ];
{
    float tlong, tshort, del, ea, eb, m, s;
    float pahsat;
            del = 1.5 * hf + sdel; /* Estimate of delay */
            kint = (0.5 * hf)/(km * del);
            ea = exp(hf/tl);
            eb = exp(hf/tin);
            m = ea * eb;
            s = ea +eb;
            kder = kint/(1.0 + m — s);
            kprop = (s — 2.0) * kder;
}
```

Exhibit B

```
/*                  Exhibit B
Measurements - see ox.txt for details.
        J. Mills, Phospho Energetics   1986 06 05
        C  Copyright, Phospho Energetics   1986.
This version has corrected and averaged pulse rate calculation.
        modified on April-10-1987   R. Pillutla, J. Taube
If the pulse rate from the oximeter goes beyond the average value by
PULSWG,
the new set of data is taken to be written onto a file. The status is
restored
when the swing is within acceptable limits.
        modified on June-16-1987   R. Pillutla, J. Taube
Pulse rate is used as a data validity detector as in 4-10-87 modifica-
tion.
However, PaO2 is used as an apnea detector and when this is sensed, ui
(FiO2) is brought to uiclimit during apnea and when HSAT (PaO2) is back to
normal, ui continues as before as in the pulse rate detector.
*/
#includes "defs.h"
#define PULSWG 0.24     /* pulse swing which est. detection window */
#define PAOSWG 10       /* blood pao limit of 10 mmHg for window */
int mes(ccon, mst. flag, hpaoflag)
float ccon[ ], mst[ ];
int flag;               /* —1 to initialise, else zero */
int *hpaoflag;          /* 1=bad: 0 = good hpao */
{
            int getdat( );
            void setint( );
            float pahsat( );
            static float sums[8+8];    /* Sums of voltages */
            float data[8];
            static int nflag;          /* 0 if waiting for data, —1 if waiting for
                                            interdata voltage. */
            int i, n, rhf;             /* reference hf */
            static int count, badcnt;    /* good & bad counts for data set */
            float pulavg;              /* pulse average */
            static float savpul;       /* save previous pulse avg */
            static float savpao;       /* save previous pao avg /*
            static int firstdata=0;    /* 1 = read data first time */
            static int firstset=0;     /* first time aquiring data */
            int base, report;          /* which part the data is stored, report
                                            the data to the monitor and a file */
/*********************** INITIALISE ***********************/
            report = 0;
            pstr = —1.0;
            *hpaoflag = 0;             /* still collecting data */
            if (flag == —1)            /* 1 = bad hpao */
            {                          /* first entry into this module */
```

Exhibit B

```
                setint(6);          /* Start data collection */
                for (i=0; i<16; i++) sums[i] = 0.0;
                count = 0;
                badcnt = 0;
                nflag = 0;
                firstdata=1;        /* collect data first time */
                firstset=1;         /* collect first set data for hpao */
        }
/****************** COLLECT DATA **************************/
        if (flag == 0)
        {
                rhf = rnd(hf);      /* hf could ohange while collecting */
                if ((n = getdat(data, 6)) > -1)
                {
                        if (nflag == 0)             /* waiting for nmr data
*/
                        {
                            if (data[4] >= 0.0)     /* found some */
                            {
                                sums[4] = data[4];
                                nflag = -1;
                            }
                        }
                        else if (data[4] < -1.0) nflag = 0; /* interdata found */
                        if (n < rhf-count) /* use only the most recent values */
                        {
                            if (firstdata == 1)     /* very first time */
                            {                       /* no part data /*
                                pulavg = data[2];
                                firstdata = 0;                  /* reset the fl
ag */
                            }
                            else if (count ==0) pulavg = savpul;
                            else pulavg = sums[2] /count;        /* not 1st or
0 count */
/******************** validate data ************************/
/****************** Setup for movement detection ***********/
                        if ((data[2] <= (pulavg + PULSWG)) && (data[2] >= (pulavg -
PULSWG)))
                                /******** pulse is good ********/
                        {
                                for (i=0; i<4; i++) sums[i] += data[i];
                                sums[5] += data[5] ;
                                count++;
                                badcnt = 0;         /* good pulse indicator */
                                base = 0;           /* good half */
                        }
                else                                /* bad pulse */
                        {                           /* bad half of array */
                                base = 8;
                                for (i=0; i<4; i++) sums[base+i] += data[i];
                                sums[base+5] += data[5];
                                badcnt++;
                        }
                }
        }
        if ((count >= rhf) || (badcnt >= rhf))       /* Enough data
                                                        collected, good or
bad */
        {
                for (i=0, i<4; i++) sums[base+i] /= rhf; /* average */
                sums[base+5] /= rhf;
                hsat = sums[base+1] * 20.0;
                pulse = sums[base+2] * 50.0;            /* 5V = 250 per
min */
                box = sums[base+3] * 20.0;
                nmr = sums[base+4] * 0.4;
                hpao = pahsat(hsat);
                bpao = pahsat(box);
                roxy = sums[base+5] * 100.0;
            if (badcnt == 0)                        /* good pulse rate /*
                {
                    if ( (hpao < savpao + PAOSWG && hpao > savpao - PAOSWG ||
                        firstset == 1) )
                    {                               /* good hpao */
                        firstset = 0;
                        savpao =hpao;
                        pstr = sums[0] * 2.0;
                        if (pstr < 0.0) pstr 0.0;
                    }
/****************** BAD HPAO ******************/
```

-continued

```
/*              Exhibit B
/*
            else
                {   printf("WARNING, patient apnea\n");

printf("or sensor has come off patient\n");
                    *hpaoflag = 1;
                }
*/
    }
    else                                    /* bad pulse rate */
{       printf("WARNING, patient movement\n");

printf("or sensor has come off petient\n");
        }
            if(nmr > 0.001) npao = 41.7 * nmr + 40.0;
            else npao = -1.0;
            for (i=0; i<8; i++) sums[base+i] = 0.0;     /* new data */
            savpul = pulavg;                            /* save pulse
avg */
        }
            report = 1;             /* complete set of data */
        }
        if (count >= rhf)
        count = 0;
        else if (badcnt >= rhf)
            {
                    badcnt = 0;
            }
    }
    return(report);
```

I claim:

1. An adaptive controller for delivering fractional inspired oxygen to a patient, said controller comprising an oximeter adapted to be connected by an optical sensor to said patient for measuring said patient's blood hemoglobin saturation and pulse rate, said oximeter generating signals representative of said blood hemoglobin saturation and said pulse rate, calculation means responsive to said signals from said oximeter for determining the fractional inspired oxygen level to be delivered to the patient, a source of oxygen, a source of air and means connected to said source for mixing oxygen and air, said means for mixing being controlled by said calculation means and having an output adapted to be connected to the patient, said calculation means controlling the oxygen concentration that said means for mixing feeds to the patient to cause the blood in the patient to reach a predetermined hemoglobin saturation level which adapts to the patient's requirements.

2. The invention of claim 1 wherein said calculation means determines blood partial pressure from the signals provided by said oximeter for enabling continuous monitoring of said patient's respiration.

3. The invention of claim 1 wherein said calculation means repeatedly determines the average pulse rate of said patient from said signals representative of said pulse rate whereby movement of said patient can be detected.

4. An adaptive controller for delivering fractional inspired oxygen to a patient, said controller comprising a detection device adapted to be connected to said patient for measuring said patient's blood hemoglobin saturation and pulse rate, said device generating signals representative of said blood hemoglobin saturation and said pulse rate, calculation means responsive to said signals from said device for determining the fractional inspired oxygen level to be delivered to the patient, a source of oxygen and a source of air and means connected to said source for mixing oxygen and air, said means for mixing being controlled by said calculation means and having an output adapted to be connected to said patient, said calculating means controlling the oxygen concentration that said means for mixing feeds the patient to cause the blood in the patient to reach a predetermined hemoglobin saturation level, said calculation means including means for determining an excess deviation of the patient's pulse rate, said means for determining an excess deviation causing said output of said calculation means to fix the fractional inspired oxygen to the patient until the excess deviation of the pulse rate has been terminated.

5. The invention of claim 4 wherein said excess deviation of said pulse rate is detected by calculation of an average pulse rate over a preset period of time and comparing incoming pulse rate to said average pulse rate to determine whether said incoming pulse rate is within a predetermined amount compared to said average pulse rate.

6. An adaptive controller for delivering fractional inspired oxygen to a patient, said controller comprising an oximeter adapted to be connected by an optical sensor to said patient for measuring said patient's blood hemoglobin saturation and pulse rate, said oximeter generating signals representative of said blood hemoglobin saturation and said pulse rate, calculation means responsive to said signals from said oximeter for determining the fractional inspired oxygen level to be delivered to the patient, a source of oxygen, a source of air and means connected to said source for mixing oxygen and air, said means for mixing being controlled by said calculation means and having an output adapted to be connected to said patient, said calculation means controlling the oxygen concentration that said means for mixing feeds to the patient to cause the blood in the patient to reach a predetermined hemoglobin saturation level, said calculation means including means for determining a depressed respiration level causing said means for mixing to provide to the patient a preset higher percentage of oxygen to the patient until the depressed respiration level of the patient has terminated.

7. The invention of claim 6 wherein said means for determining a depressed respiration level (includes) means for calculating the average partial pressure of blood for a preset period of time and comparing incoming blood partial pressure with said average blood partial pressure to determine whether said incoming blood part pressure is within a predetermined amount with respect to said average.

* * * * *